United States Patent [19]

de Schrijver

[11] 4,316,883

[45] Feb. 23, 1982

[54] RADIOACTIVE COMPOSITION

[75] Inventor: Marc de Schrijver, Rosenau, France

[73] Assignee: Solco Basel AG., Basel, Switzerland

[21] Appl. No.: 883,421

[22] Filed: Feb. 21, 1978

Related U.S. Application Data

[63] Continuation of Ser. No. 797,664, May 17, 1977, abandoned.

[30] Foreign Application Priority Data

May 31, 1976 [CH] Switzerland .......................... 6793/76

[51] Int. Cl.$^3$ ...................... A61K 49/00; A61K 43/00
[52] U.S. Cl. .................................... 424/1; 260/429 R; 260/429.7; 424/9; 424/313; 562/433
[58] Field of Search .................... 424/1, 1.5, 9, 313; 540/20, 22, 156, 196, 127, 136; 260/518 R, 515 P, 429

[56] References Cited

U.S. PATENT DOCUMENTS

| | | | |
|---|---|---|---|
| 3,981,980 | 9/1976 | Baker et al. | 424/1 |
| 4,017,596 | 4/1977 | Loberg et al. | 424/1 |
| 4,027,005 | 5/1977 | Adler et al. | 424/1 |

OTHER PUBLICATIONS

Wistow et al., J. Nuc. Med., vol. 17, No. 6, 1976, p. 545.

*Primary Examiner*—Christine M. Nucker
*Attorney, Agent, or Firm*—Ladas & Parry

[57] ABSTRACT

A radioactive composition for the scintigraphic imaging of the hepatobiliary system is disclosed, the composition comprising a complex of $^{99m}$Tc with a [2,6-di(-lower)alkyl or 2,4,6-tri(lower)alkyl-acetanilido]-iminodiacetic acid having a total of at least 3 carbon atoms in the alkyl groups, or a salt thereof, in sterile aqueous solution. In a preferred composition the complex contains in addition a tin salt and is prepared directly prior to use by reacting NaTcO$_4$ with SnCl$_2$ and the iminodiacetic acid.

9 Claims, No Drawings

RADIOACTIVE COMPOSITION

This is a continuation of application Ser. No. 797,664 filed May 17, 1977, abandoned.

The present invention relates to a novel radioactive composition for the scintigraphic (static or in particular dynamic) visualization of the hepatobiliary system (liver, gall bladder and biliary tract).

Compositions which are cleared largely through the liver into the biliary tract and from there into the intestine are known as hepatobiliary agents. Radioactive compositions of this kind now play an important part in the diagnosis of disorders of this system. They allow—by means of a number of images produced over a given period—an exact assessment of hepatobiliary function and in particular of hepatobiliary transport.

These radiopharmaceuticals are considered to behave as follows in vivo. After intravenous injection they are carried around the body in the blood. At the same time they begin to be cleared from the circulatory system by the liver and passed through the biliary tract into the intestine as well as being eliminated by the kidneys and passed into the urinary tract. In the absence of renal excretion, measurement of the rate of disappearance of the radioactive agent from the circulatory system gives a quantitative indication of liver function. All prior art hepatobiliary radiopharmaceuticals are excreted to a certain extent through the kidneys however.

Up to now $^{131}$I—labelled agents have been used for the diagnosis of hepatobiliary disorders, in particular $^{131}$I-rose bengal (dichlorotetra-$^{131}$I-fluorescein), diphenyl-$^{131}$I-iodonium sulphate, Iodipamide-I$^{131}$ and Bromsulfan-I$^{131}$. A better agent has been sought for some time. Desirable features would be e.g. a higher concentration in the bile, more rapid excretion through the liver and above all low exposure of the patient to radiation.

In fact $^{131}$I has a half-life of 8.05 days and emits 42% non-penetrating, i.e. diagnostically worthless, and 15% possibly usable radiation. The relevance of these figures for the patient is readily apparent from the following. A typical case is when the liver ceases to function or when the hepatobiliary route becomes mechanically blocked. Both cases result in slower clearance of the radiopharmaceutical from the blood, i.e. its accumulation in the circulatory system. In the absence of compensatory renal excretion (which is in fact desirable on diagnostic grounds), this accumulation causes a longer residence time in the body and hence the patient receives a radiation dose which is about 10 to 100 times greater than in healthy individuals.

A novel hepatobiliary radiopharmaceutical has now been discovered which possesses properties qualitatively similar to those of $^{131}$I-rose bengal but which fulfills the requirements more satisfactorily.

The composition of the present invention comprises a complex of $^{99m}$Tc with a dicarboxylic acid of the formula:

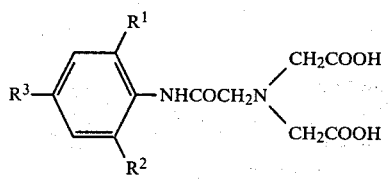

in which at least two of the symbols $R^1$, $R^2$ and $R^3$ are lower alkyl groups having 1 to 4 carbon atoms, the third is hydrogen or a lower alkyl group having 1 to 4 carbon atoms and the three symbols contain a total of at least 3 carbon atoms, or one of its water-soluble salts, in sterile, aqueous solution.

Most suited as the water-soluble salts of the dicarboxylic acid are the alkali metal salts, preferably the sodium salt.

Particularly preferred dicarboxylic acids of the above formula are (2,6-diethylacetanilido)-iminodiacetic acid ($R^1$ and $R^2 = C_2H_5$, $R^3 = H$), (2,6-diisopropylacetanilido)-iminodiacetic acid ($R^1$ and $R^2 = i-C_3H_7$, $R^3 = H$) and (2,4,6-trimethylacetanilido)-iminodiacetic acid ($R^1$, $R^2$ and $R^3 = CH_3$).

The method of preparing the composition comprises, in principle, allowing an aqueous solution containing $^{99m}$Tc ions to react with the dicarboxylic acid or a water-soluble salt thereof.

The pertechnetates, above all sodium $^{99m}$Tc-pertechnetate, are the $^{99m}$Tc compounds customarily used since these are virtually the only ones commercially available. A pertechnetate solution may be obtained by means of a $^{99}$Mo/$^{99m}$Tc generator. Eluates obtained from such a generator usually have a relatively low specific activity (less than 5 mCi/ml). Although sufficient for static scintigraphy, this is too low for dynamic studies such as the sequence imaging of the hepatobiliary system. These eluates thus have to be processed to solutions of higher specific activity. A suitable procedure is extraction with methyl ethyl ketone, evaporation of the solvent and dissolution of the residue in saline—see Journal of Nuclear Medicine 11 (1970), 386. A far simpler method has however been disclosed recently in U.S. Pat. No. 3,961,038 to the present applicant. A quite different approach involves the use of a $^{99}$Mo/$^{99m}$Tc generator of higher activity (300 to 500 mCi). Fractional elution from such generators gives during the first few days pertechnetate solutions of sufficiently high specific activity (10 to 15 mCi/ml) but these generators are of course correspondingly expensive.

To prepare the novel composition, the 7-valent $^{99m}$Tc in the pertechnetate must however be reduced to a lower valency. The reduction may be carried out by various methods, e.g. electrolytically or by means of reducing agents.

Reduction by means of a tin(II) salt, preferably tin(II) chloride, has been found to be particularly simple and convenient. The complex in the composition thus obtained will accordingly also contain a tin salt, tin chloride in the preferred embodiment.

Whether the composition contains a simple $^{99m}$Tc complex or a double complex of $^{99m}$Tc and Sn, it possesses a decisive advantage over prior art, $^{131}$I-labelled radio-pharmaceuticals. $^{99m}$Tc has a half-life of only 6 hours and only 13% of the radiation emitted is non-penetrating and hence diagnostically worthless. The radiation dose received by the patient is therefore reduced to a fraction of that caused by conventional imaging agents which is of particular significance for children.

The short half-life of $^{99m}$Tc does however make it necessary to prepare the composition immediately before use, i.e. shortly before its intravenous injection. This is made possible by the preferred embodiment of the method of the invention described below.

A sterile aqueous solution of a pertechnetate, preferably sodium $^{99m}$Tc-pertechnetate, is prepared containing the amount of radioactivity calculated for the patient. This amount may be 5–50 miCi but is preferably 10–20 mCi. The other components of the complex, i.e. the dicarboxylic acid or a water-soluble salt thereof and a tin(II) salt, preferably tin(II) chloride, are dissolved together in water. The pH of the resulting solution is adjusted to a suitable value between about 5.5 and 6.5 and the solution sterilised, preferably by sterilising filtration. The solution can be stored in this form, under oxygen-free conditions of course, for long periods without deterioration. The shelf life can be lengthened however by converting the solution to an anhydrous powder. This is best done by freeze-drying. In this state the mixture can be kept for months.

In the preferred embodiment it is the abovedescribed two aqueous solutions or the pertechnetate solution and the freeze-dried or otherwise dried solid mixture which represent the starting materials for the direct preparation of the composition. Mere mixing of the two solutions or the pertechnetate solution and the solid mixture gives a composition which is ready for immediate administration. The composition can therefore be prepared at the patient's bedside so to speak.

Provision of the reagents intended for reaction with the pertechnetate in an easily usable form which is stable over long periods considerably simplifies the use of the composition. The above-described sterile aqueous solution and the corresponding sterile, anhydrous, solid mixture (the dicarboxylic acid or its water-soluble salt and the tin(II) salt) thus also form part of the invention as means for carrying out the method of the invention. Their preparation is described below in detail using tin(II) chloride as the tin(II) salt.

The dicarboxylic acid is stirred into water and 1 N caustic soda solution added to the mixture with continuous stirring until the pH is 7.5 to 8.5. This dissolves the dicarboxylic acid completely. The pH is then brought slowly down to about 6.5 by the careful, drowise addition of dilute hydrochloric acid with stirring. The solution is filtered through a sterilising filter with a pore size of 0.22μ and as small a volume as possible of tin(II) chloride solution in 1 N or more dilute hydrochloric acid added very slowly with vigorous stirring. Finally the pH of the solution is adjusted to 5.5 to 5.7 and the solution introduced into ampoules. Oxygen is removed from the ampoules which may then either be sealed with the solution inside them or the solution freeze-dried before the ampoule is sealed.

An ampoule filled and sealed in this way may for instance contain 20 to 25 mg of dicarboxylic acid and up to 100 or 200 μg of $SnCl_2 \cdot 2H_2O$ as the reducing agent, or 40 mg of dicarboxylic acid and up to 100 or 200 μg $SnCl_2 \cdot 2H_2O$ in solid form or in e.g. 4 ml of solution.

Analysis of the composition by reacting the contents of the ampoule with a solution of sodium $^{99m}$Tc-pertechnetate shows that labelling proceeds practically quantitatively, giving yields of over 98%. Less than 5% of the radioactivity in the composition is present as colloid.

Preliminary studies in animals have been carried out with the complex made from (2,6-diethylacetanilido)iminodiacetic acid, tin(II) chloride and sodium $^{99m}$Tc-pertechnetate. The complex was compared with $^{131}$I-rose bengal using a baboon model.

Clearance of the composition of the invention from the blood was about twice as rapid as clearance of $^{131}$I-rose bengal. After 1 hour only traces of the novel composition (less than 1% of the administered dose) remained in the blood. After 1 hour about 3% of the $^{131}$I-rose bengal remained and even after 3 hours about 2% remained.

During the first 30 minutes after administration, the concentration of the composition in the bile was several (over four) times that of $^{131}$I-rose bengal. The concentration decreased slowly with time, but was still ⅓ higher than that of $^{131}$I-rose bengal after 3 hours.

The rates of urinary excretion of the two compositions were similar, both increasing steadily, although that of the novel composition more slowly. After 3 hours almost 5% of the administered dose of the novel composition had been excreted in the urine compared with about 2% for $^{131}$I-rose bengal.

As well as the benefits derived by the patient as a result of the low radiation dose mentioned above, the novel composition possesses two further advantages over the best known prior art composition. The novel composition is cleared more rapidly from the blood and it localizes more rapidly and in much larger quantities in the hepatobiliary system.

Since the dicarboxylic acids of the formula given above are novel compounds, a method of preparing them will now be described.

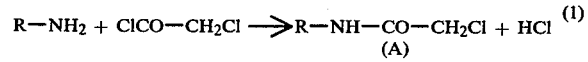
(A)

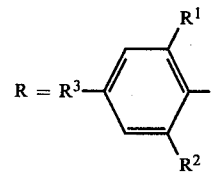

The substituted aniline is dissolved in anhydrous acetone in the proportions 100 g:100 to 200 ml acetone. The resulting solution is placed in a dropping funnel. A reaction flask containing a 10% molar excess (based on the substituted aniline) of freshly prepared choroacetyl chloride is placed in an ice bath to cool. The solution of the aniline is then slowly added dropwise with continuous stirring and continued cooling. When all the aniline has been added the mixture is stirred for 30 minutes and sufficient water added to hydrolyze excess chloroacetyl chloride. The mixture is stirred again for 10 minutes and placed if necessary in a larger reaction vessel.

It should be noted that the aniline also acts as an acid binding agent so that only half of it is converted into the compound of formula A above, the other half remaining in the reaction mixture as aniline hydrochloride. This can be remedied by using another acid binding agent, but this makes working up compound A difficult.

0.1 N hydrochloric acid in 10 to 20 times its volume of acetone is added to the mixture and stirred in vigorously. Compound A separates as a solid. The chloroacetic acid is readily soluble in 0.1 N hydrochloric acid and can be removed by filtration. Compound A is rinsed twice with a large volume of 0.1 N hydrochloric acid and purified by recrystallisation from aqueous 50 to 80% ethanol. The pure crystals of compound A should be white to pale yellow in color.

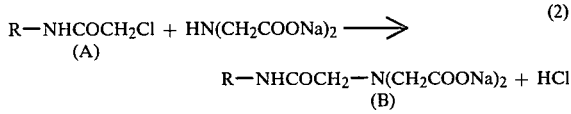

$$R-NHCOCH_2Cl + HN(CH_2COONa)_2 \longrightarrow \quad (2)$$
(A)
$$R-NHCOCH_2-N(CH_2COONa)_2 + HCl$$
(B)

The desired amount of compound A is dissolved in as little absolute alcohol as possible. In addition, a 100% excess of iminodiacetic acid in a solution of the molar equivalent of sodium hydroxide is dissolved in a small volume of water. To this aqueous solution is added an equimolar quantity of sodium carbonate (based on compound A). The two solutions are mixed together and heated for at least 12 hours at 80° C. under reflux.

On completion of the reaction, a small quantity of water corresponding to half the volume of the alcohol originally used is added to the mixture. The alcohol is then evaporated off completely under reduced pressure. A second small amount of water is added and the solution filtered to remove unreacted compound A. The filtrate contains the desired compound B as its disodium salt, and other salts. At this stage of the procedure the formation of a gum-like or oily, water-insoluble phase may be observed, depending on the purity of the starting materials. This phase can be easily separated from the aqueous phase by extracting several times with diethyl ether until a clear solution is obtained. Any diethyl ether remaining should be removed by warming the solution before compound B is isolated.

To isolate compound B, the pH of the solution is lowered over 30 minutes to 1.5 to 2.0 by slowly adding hydrochloric acid with stirring. The precipitate is filtered off and washed twice with cold 0.025 N hydrochloric acid.

The product may be purified as follows. The compound is dissolved in very dilute sodium hydroxide solution at pH 8 to 8.5. On stirring vigorously, a clear solution is obtained. If the solution is not clear, it is filtered. A volume of acetone corresponding to 20% of that of the solution is added and mixed in vigorously. The pH is reduced slowly to 2.0 by adding 5 N hydrochloric acid and the solution stirred at this pH for at least 2 hours. During this period, the compound precipitates out very slowly and can be filtered off. If the product is not pure white, the above purificator procedure is repeated. The last purification is carried out in aqueous solution, without the addition of any acetone. The product is finally dried under reduced pressure.

The following compounds have been prepared by the above method:
(2,6-diethylacetanilido)-iminodiacetic acid, mp 176°–178° C.;
(2,6-diisopropylacetanilido)-iminodiacetic acid, mp 166°–175° C.; (2,4,6-trimethylacetanilido)-iminodiacetic acid, mp 200°–210° C.

As the free dicarboxylic acid, all are insoluble in water.

What is claimed is:

1. A radioactive composition for the scintigraphic imaging of the hepatobiliary system, the composition comprising a complex of $^{99m}Tc$ with a dicarboxylic acid of the formula:

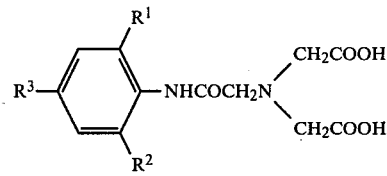

in which $R^1$ and $R^2$ are each an ethyl or an isopropyl group, and $R^3$ is hydrogen, or each of $R^1$, $R^2$ and $R^3$ are a methyl group, or one of its water-soluble salts, in sterile, aqueous solution.

2. The composition of claim 1 wherein $R^1$, $R^2$ and $R^3$ are each a methyl group.

3. The composition of claim 1 further comprising tin chloride as a component of the complex.

4. The composition of claim 1 wherein the dicarboxylic acid is present as its sodium salt.

5. The composition of claim 1 further comprising a tin salt as a component of the complex.

6. A method of preparing the composition of claim 1, the method comprising allowing the dicarboxylic acid defined in claim 1, or a water-soluble salt thereof, to react under sterile conditions with an aqueous solution containing $^{99m}Tc$ ions.

7. The method of claim 8 wherein the dicarboxylic acid or the water-soluble salt thereof is allowed to react with an aqueous $^{99m}Tc$-pertechnetate solution in the presence of a tin(II) salt.

8. The method of claim 7 wherein the $^{99m}Tc$-pertechnetate solution is a solution of sodium $^{99m}Tc$-pertechnetate and the tin(II) salt is tin(II) chloride.

9. A method for imaging the hepatobiliary system comprising injecting the composition of claim 1 and subsequently scanning the body for radioactivity.

* * * * *